(12) United States Patent
Hu et al.

(10) Patent No.: US 9,747,688 B2
(45) Date of Patent: *Aug. 29, 2017

(54) SURFACE AND IMAGE INTEGRATION FOR MODEL EVALUATION AND LANDMARK DETERMINATION

(71) Applicant: Smith & Nephew, Inc., Memphis, TN (US)

(72) Inventors: Yangqiu Hu, Lewis Center, OH (US); Gaetano Calabrese, Aarau (CH)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/277,328

(22) Filed: Sep. 27, 2016

(65) Prior Publication Data

US 2017/0018082 A1    Jan. 19, 2017

Related U.S. Application Data

(63) Continuation of application No. 14/270,326, filed on May 5, 2014, now Pat. No. 9,454,643.

(Continued)

(51) Int. Cl.
*G06K 9/00* (2006.01)
*G06T 7/00* (2017.01)
(Continued)

(52) U.S. Cl.
CPC .......... *G06T 7/0014* (2013.01); *G06F 19/321* (2013.01); *G06T 7/174* (2017.01);
(Continued)

(58) Field of Classification Search
None
See application file for complete search history.

(56) References Cited

U.S. PATENT DOCUMENTS

| 4,908,573 A | 3/1990 | Kaufman et al. |
| 6,178,220 B1 | 1/2001 | Freundlich et al. |

(Continued)

FOREIGN PATENT DOCUMENTS

| WO | 2005036457 A2 | 4/2005 |
| WO | 2012027185 A1 | 3/2012 |

OTHER PUBLICATIONS

"Slicer User Guide"; Jul. 10, 2012 (Jul. 10, 2012), pp. 17-25, XP055172537; Retrieved from the Internet: URL:https://web.archive.orgjweb/20120710014854/http://www.slicer.orgjarchivesjusers/index.html [retrieved on Feb. 27, 2015], pp. 24-25.

(Continued)

*Primary Examiner* — Shervin Nakhjavan
(74) *Attorney, Agent, or Firm* — Taft Stettinius & Hollister LLP

(57) ABSTRACT

Embodiments of the present disclosure provide a software program that displays both a volume as images and segmentation results as surface models in 3D. Multiple 2D slices are extracted from the 3D volume. The 2D slices may be interactively rotated by the user to best follow an oblique structure. The 2D slices can "cut" the surface models from the segmentation so that only half of the models are displayed. The border curves resulting from the cuts are displayed in the 2D slices. The user may click a point on the surface model to designate a landmark point. The corresponding location of the point is highlighted in the 2D slices. A 2D slice can be reoriented such that the line lies in the slice. The user can then further evaluate or refine the landmark points based on both surface and image information.

20 Claims, 12 Drawing Sheets

Related U.S. Application Data

(60) Provisional application No. 61/818,541, filed on May 2, 2013.

(51) Int. Cl.

| | | |
|---|---|---|
| *G06F 19/00* | (2011.01) | |
| *G06T 17/20* | (2006.01) | |
| *G06T 19/20* | (2011.01) | |
| *G06T 19/00* | (2011.01) | |
| *G06T 15/08* | (2011.01) | |
| *G06T 7/174* | (2017.01) | |

(52) U.S. Cl.
CPC .............. *G06T 15/08* (2013.01); *G06T 17/20* (2013.01); *G06T 19/00* (2013.01); *G06T 19/20* (2013.01); *G06T 7/0012* (2013.01); *G06T 2207/10024* (2013.01); *G06T 2207/10081* (2013.01); *G06T 2207/10088* (2013.01); *G06T 2207/20021* (2013.01); *G06T 2207/30008* (2013.01); *G06T 2207/30204* (2013.01); *G06T 2210/41* (2013.01); *G06T 2219/008* (2013.01); *G06T 2219/028* (2013.01)

(56) References Cited

U.S. PATENT DOCUMENTS

| | | | | |
|---|---|---|---|---|
| 6,450,978 | B1* | 9/2002 | Brosseau | A61B 90/36 600/595 |
| 6,998,841 | B1 | 2/2006 | Tamez-Pena et al. | |
| 7,155,042 | B1* | 12/2006 | Cowan | A61B 5/055 382/128 |
| 2007/0276214 | A1 | 11/2007 | Dachille et al. | |
| 2008/0137927 | A1* | 6/2008 | Altmann | A61B 8/4488 382/131 |
| 2008/0225044 | A1 | 9/2008 | Huang et al. | |
| 2009/0138020 | A1* | 5/2009 | Park | A61B 5/055 606/88 |
| 2009/0190815 | A1 | 7/2009 | Dam et al. | |
| 2009/0222016 | A1 | 9/2009 | Park et al. | |
| 2009/0226067 | A1 | 9/2009 | Souza et al. | |
| 2010/0156904 | A1* | 6/2010 | Hartung | G06T 17/00 345/420 |
| 2010/0240996 | A1* | 9/2010 | Ionasec | G06T 7/0016 600/443 |
| 2010/0312096 | A1* | 12/2010 | Guttman | A61B 34/20 600/411 |
| 2010/0315424 | A1* | 12/2010 | Cai | G06T 17/00 345/427 |
| 2012/0002840 | A1* | 1/2012 | Linnenbank | G06K 9/32 382/103 |
| 2013/0089253 | A1* | 4/2013 | Chabanas | G06T 17/30 382/131 |
| 2013/0121551 | A1* | 5/2013 | Poulsen | A61N 5/1049 382/131 |
| 2013/0197870 | A1* | 8/2013 | Steines | A61B 17/1675 703/1 |

OTHER PUBLICATIONS

Cebral et al.; "From Medical Images to Anatomically Accurate Finite Element Grids;" International Journal of Numerical Methods in Engineering; Chichester, GB; 51(6):985-1008 (2001); vol. 51 No. 8; Jul. 20, 2001; pp. 985-1008; XP008037771; ISSN: 0029-5981; DO: 10.1002/NME.205 abstract.

Jakab et al.; "A Practical Guide to the 3D Slicer;" Internet Citation: Feb. 2001; XP002290128: Retrieved from the Internet: URL: http://spl.bwh.harvard.edu:8000/pages; papers/slicer/manual/slicer manual.htm [retrieved on Jul. 27, 2004; pp. 2-4.

Li et al.; "Human Hip Joint Cartilage: MRI Quantitative Thickness and Volume Measurements Discriminating Acetabulum and Femoral Head;" IEEE Transactions on Biomedical Engineering; 55(12); 2008; pp. 2731-2740.

Xing et al.; "Automatically Assessing Limb Alignment and Hip Fracture Using 3D Models;" IEEE Computing in Science & Engineering; 15;(2): 2013; pp. 10-20.

International Search Report and Written Opinion for PCT/US2014/036867 dated Sep. 17, 2014.

International Search Report and Written Opinion for PCT/IB2014/000757 dated Mar. 13, 2015.

* cited by examiner

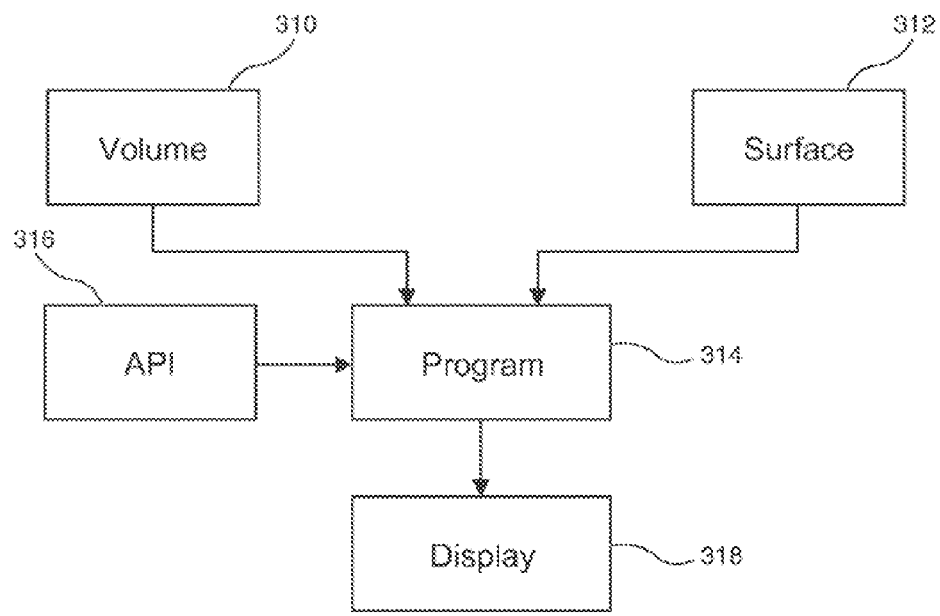
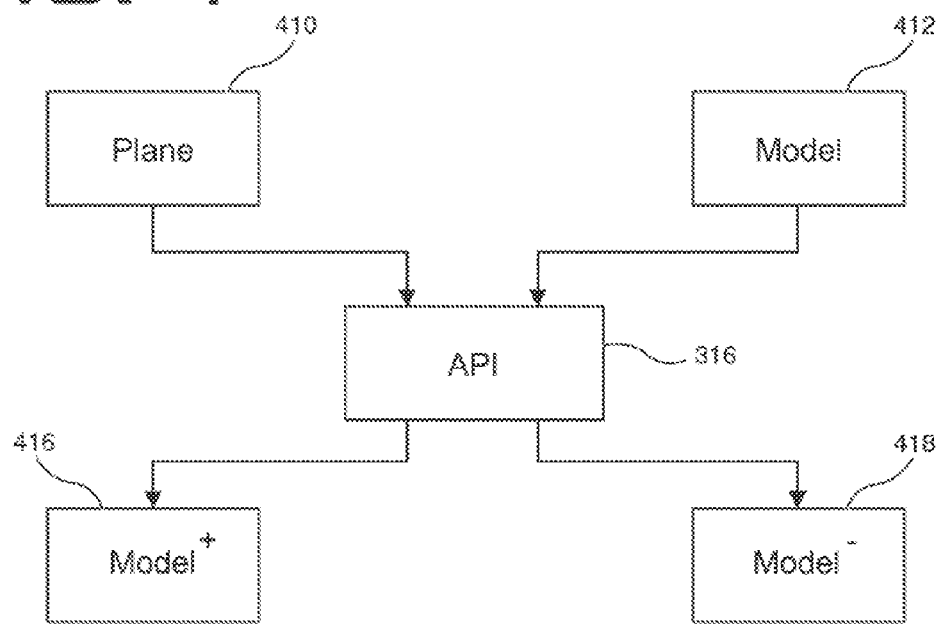

SURFACE AND IMAGE INTEGRATION FOR MODEL EVALUATION AND LANDMARK DETERMINATION

CROSS-REFERENCE TO RELATED APPLICATION

This application is a continuation of U.S. patent application Ser. No. 14/270,326, filed on May 5, 2014, which claims the benefit of U.S. Provisional Application No. 61/818,541, filed on May 2, 2013, the disclosure of each of these applications hereby incorporated herein by reference in its entirety.

BACKGROUND

Patient specific modeling is used in connection with surgical and orthopedic procedures to plan a surgery or to design instruments and implants for the surgery. A patient specific model allows a surgeon to account for variation in anatomy between patients by first modeling the portion of the body at which the surgery is carried out. The surgical procedure can be precisely planned by tailoring the approach and instruments to particular variations in the patient's anatomy that may otherwise cause difficulties during a standard procedure. As a first step in the process, the patient's anatomy is imaged by standard medical technology, for example using an MRI or a CT scanning machine, in order to obtain a data set that is representative of the patient's anatomy. The data set that is obtained indicates any particular variations or nuances in the patient's anatomy, and processing that data can provide a surgeon with a detailed map of the relevant body portion ahead of time.

The imaging data obtained from the patient's anatomy is processed to create a model of the patient's anatomy that is used to plan the procedure. The raw data set can be processed in a number of different ways, including filtering, interpolation, sampling, and other data processing procedures that turn the data into a digital anatomy model for the surgeon's use. One particular processing approach is image segmentation, in which the full data set is analyzed in blocks, with each block representing a different area of the relevant anatomy. These processing techniques, including segmentation, can introduce errors into the model as a result of the estimation that compresses and otherwise processes the data. For example, there may be rounding or smoothing effects that create a smooth surface in the model that does not account for the deviations from that smooth surface that are actually present in the patient's anatomy.

For some procedures, patient implants and instrumentation such as surgical guides are designed to match a specific patient's bone anatomy. In these cases, accurate models can be helpful to create an implant or surgical guide that will closely interlace with the patient's bone. Any deviations or variations between, the model and the actual anatomy, particularly in areas where the implant or surgical guide interfaces with the bone, may reduce the effectiveness of the surgical procedure. For such applications, it would be helpful to have an indication not only of the patient's estimated anatomy, but also an indication of how closely the modeled anatomy maps to the real anatomy.

SUMMARY

Disclosed herein are systems, devices, and methods for surface and image integration for model evaluation and landmark determination. Embodiments of the present disclosure provide a software program that displays both a volume as images and segmentation results as surface models in 3D together as an integrated image. Multiple 2D slices can be extracted from the 3D volume. The 2D slices can "cut" the surface models from the segmentation so that only a portion (e.g., half) of the models are displayed. The border curves resulting from the cuts are displayed in the 2D slices, enabling evaluation of surface accuracy against the raw image data in any plane. Additionally, the systems, devices and methods may allow a user to select a point on a surface model to designate a landmark point.

According to one aspect, a method for determining the accuracy of image segmentation, includes receiving raw image data representative of a patient's joint, processing the image data to create a three-dimensional surface model of a portion of the patient's joint, displaying the raw image data and the surface model together on a monitor as an integrated image, intersecting the integrated image with a plane oblique to the raw image data, and comparing the intersection of the raw image data and the plane with the intersection of the surface model and the plane. The raw image data may be captured along a patient's transverse plane, sagittal plane, or coronal plane. The raw image data and the surface model may be displayed using different respective colors. In certain implementations, the processing includes image filtering or enhancement followed by image segmentation followed by surface triangulation.

In certain implementations, the method includes selectively removing the three-dimensional surface model from the display. In certain implementations, processing the image data includes deriving image data by interpolating between image slices. In certain implementations, the method also includes re-segmenting the raw image data and recreating a three-dimensional surface model of a portion of the patient's joint. In certain implementations, the method includes placing a marker or line on the surface model of the patient's joint. In certain implementations, the marker is placed on a visual representation of the patient's distal femoral epicondyles and a line is drawn through the condyles. In certain implementations, after the line is drawn, a plane oblique to the raw image data is reoriented such that the line lies within the plane. In certain implementations, the method includes identifying anatomic landmarks on the surface model. In certain implementations, the method includes identifying ligament attachment points on the surface model.

According to another aspect, a system for determining the accuracy of image segmentation includes a processor configured to receive raw image data representative of a patient's joint, process the image data to create a three-dimensional surface model of a portion of the patient's joint, intersect the integrated image with a plane oblique to the raw image data, and compare the intersection of the raw image data and the plane with the intersection of the surface model and the plane, and a monitor configured to display the raw image data and the surface model together on a monitor as an integrated image, in certain implementations, the raw image data is captured along a patient's transverse plane, sagittal plane, or coronal plane. In certain implementations, the raw image data and the surface model are displayed using different respective colors. In certain implementations, processing the image data comprises image filtering or enhancement followed by image segmentation followed by surface triangulation.

In certain implementations, the processor is further configured to selectively remove the three-dimensional surface model from the display. In certain implementations, processing the image data includes deriving image data by interpolating between image slices. In certain implementations, the processor is further configured to re-segment the raw image data and recreate a three-dimensional surface model of a portion of the patient's joint.

In certain implementations, the processor is further configured to place a marker or line on the surface model of the patient's joint. The marker may be placed on a visual representation of the patient's distal femoral epicondyles and a line may be drawn through the condyles. After the line is drawn, a plane oblique to the raw image data may be reoriented such that the line lies within the plane. In certain implementations, the processor is further configured to identify anatomic landmarks on the surface model. In certain implementations, the processor is further configured to identify ligament attachment points on the surface model.

According to another aspect, a system for determining the accuracy of image segmentation includes means for receiving raw image data representative of a patient's joint, means for processing the image data to create a three-dimensional surface model of a portion of the patient's joint, means for displaying the raw image data and the surface model together on a monitor as an integrated image, means for intersecting the integrated image with a plane oblique to the raw image data, and means for comparing the intersection of the raw image data and the plane with the intersection of the surface model and the plane. The received raw image data may be captured along a patient's transverse plane, sagittal plane, or coronal plane. The raw image data and the surface model are displayed using different respective colors. In certain implementations, processing the image data comprises image filtering or enhancement followed by image segmentation followed by surface triangulation.

In certain implementations, the system includes means for selectively removing the three-dimensional surface model from the display. Processing the image data may include deriving image data by interpolating between image slices. In certain implementations, the system includes means for re-segmenting the raw image data and recreating a three-dimensional surface model of a portion of the patient's joint. In certain implementations, the system includes means for placing a marker or line on the surface model of the patient's joint. The marker may be placed on a visual representation of the patient's distal femoral epicondyles and a line may be drawn through the condyles. After the line is drawn, a plane oblique to the raw image data may be reoriented such that the line lies within the plane. In certain implementations, the system includes means for identifying anatomic landmarks on the surface model. In certain implementations, the system includes means for identifying ligament attachment points on the surface model.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIGS. 3-5 show illustrative software elements for modifying the surface model of FIG. 1 and creating border curves;

DETAILED DESCRIPTION

Figure 1:
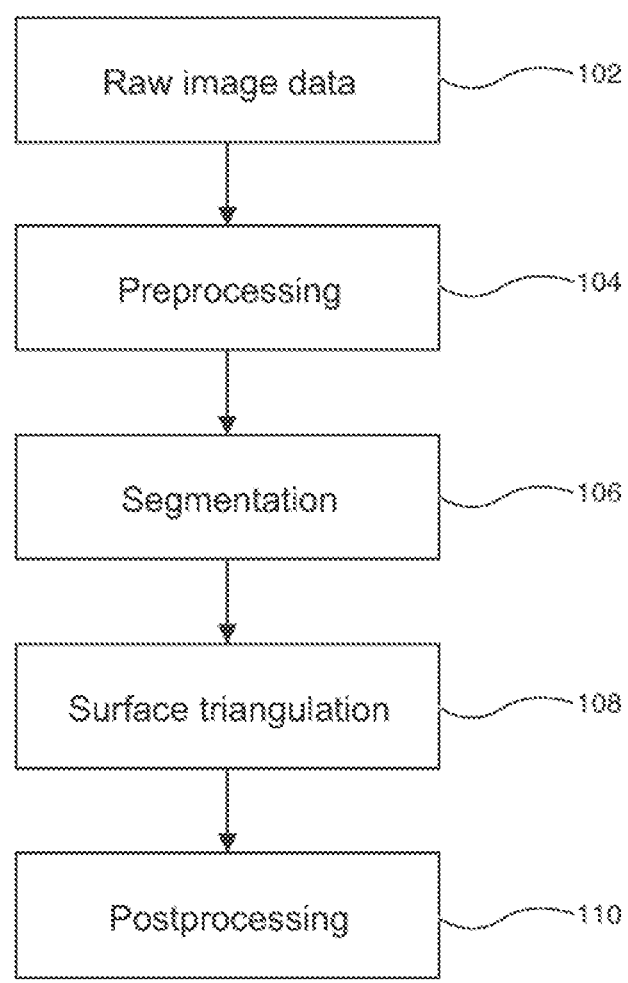
FIG. 1 shows illustrative steps to process raw image data into a surface model.

To provide an overall understanding of the systems, devices, and methods described herein, certain illustrative embodiments will be described. Although the embodiments and features described herein are specifically described for use in connection with identifying anatomical landmarks in image data for a patient's knee joint, it will be understood that the approaches disclosed are applicable to other anatomical joints as well. Moreover, the approaches outlined below may be applied to preparing patient-matched medical devices and implants to be used in surgical procedures including, but not limited to, knee, acetabular, spine arthroplasty, cranio-maxillofacial surgical procedures, shoulder arthroplasty, as well as foot, ankle, hand, and other extremity procedures. The following description of the depicted embodiment(s) is merely exemplary in nature and is in no way intended as limiting.

Embodiments of the present invention provide a software program that displays both a volume as images and segmentation results as surface models in 3D together as an integrated image. Multiple 2D slices can be extracted from the 3D volume. The 2D slices may have different locations and orientations and also may be moved using a mouse, touchscreen, and/or keyboard by a user. The 2D slices may be interactively rotated by the user to best follow an oblique structure. The 2D slices can "cut" the surface models from the segmentation so that only half of the models are displayed. The border curves resulting from the cuts are displayed in the 2D slices, enabling evaluation of surface accuracy against the raw image data in any plane. The user may click a point on the surface model to designate a landmark point. The corresponding location of the point is highlighted in the 2D slices. A user may pick two landmark points to determine a line and a 2D slice is reoriented such that the line lies in the slice. The user can then further evaluate/refine the landmark points based on both surface and image information. Alternatively, a user may draw a line by hand and a 2D slice is reoriented such that the line lies in the slice. For example, a user may trace Whiteside's line by hand.

In some embodiments, the software program may be used to determine the best landmarks for implant positioning. For example, if the posterior-most point of the condyles has cartilage damage, it might be difficult to determine the original surface of the cartilage and the plane orthogonal to the mechanical axis. The 2D slices may be moved using a mouse, touchscreen, and/or keyboard by a user. The 2D slices may be interactively rotated by the user to view different landmarks. The 2D slices can "cut" the surface models from the segmentation so that only half of the models are displayed relative to different landmarks. The border curves resulting from the cuts are displayed in the 2D slices, enabling evaluation of surface accuracy in the area of different landmarks against the raw image data in any plane.

In one particular embodiment, displaying both the volume data and the surface model allows for the evaluation of osteophytes. The evaluation of osteophytes may be used in the area of patient matched instruments and/or patient matched implants. A patient matched instrument, such, as a femoral custom cutting block, may accommodate bone osteophytes. The implant, however, whether standard or patient matched, should not be mounted on an osteophyte. Thus, the patient matched instrument may be designed to "fit" any osteophytes, but the osteophyte may be removed or the implant may be reshaped for "fit" of the implant. The 2D slices can "cut" the surface models from the segmentation so that only half of the models are displayed relative to bone and/or bone osteophytes. The border curves resulting from the cuts are displayed in the 2D slices, enabling evaluation of surface accuracy in the area of potential bone osteophytes against the raw image data in any plane.

FIG. 1 illustrates the steps for creating a surface model based upon individual patient data according to certain embodiments. At step 102, the information concerning the particular patient for the orthopedic procedure is received. In some instances, this received information includes data obtained by imaging the particular patient's joint (e.g., the knee joint of interest). Any suitable imaging technology may be used to obtain this data, including, without limitation, MRI, x-ray, CT, ultrasound, or combinations thereof. In certain embodiments, non-image based technologies may be used to obtain data about the patient's joint.

In the particular embodiment illustrated, the information received at step 102 includes one or both of DICOM raw data as well as processed data obtained from an MRI. In this particular embodiment, this data includes sufficient information to identify and characterize in three dimensions relevant surfaces and other features of the patient's anatomy. Non-limiting examples of such surfaces and other features include articular surfaces of the femur, tibia, and patella (e.g. medial and lateral condylar surfaces on the femur and corresponding articular surfaces on the tibia, the trochlear groove on the femur and corresponding articular surfaces on the patella), non-articular surfaces of such anatomy, and other features of such anatomy (e.g. tibial tubercle, tibial eminence). In some embodiments, the MRI data may be sufficient to identify bone surfaces, cartilage surfaces, bone/cartilage interfaces, or other interfaces between different tissues and structures of the anatomy.

In this particular embodiment, the DICOM raw data and/or processed data obtained from the MRI also includes sufficient detail to distinguish and locate in three dimensions locations (e.g. points or areas) where soft tissues (e.g. ligaments and/or tendons) attach to the bony anatomy. Such attachment locations may include in embodiments related to knee arthroplasty, without limitation, attachment locations of the anterior and posterior cruciate ligaments, deep and superficial attachment locations of the medial collateral ligament, attachment locations of the lateral collateral ligament, insertion locations of the popliteal tendon/muscle, the iliotibial band insertion location, the patellar ligament attachment locations, and the quad tendon insertion location on the patella.

In some embodiments, an MRI scan protocol with specific scan parameters (e.g. the field of view (FOV), slice thickness, matrix, field strength, scan plane, scan time, bandwidth, etc.) is utilized to accurately produce detailed images of biological structures of interest (tendons, ligaments, muscles, cartilage and bones). The MRI scan may be performed with the patient lying supine, feet first with his or her leg in full extension and knee joint straight. In some embodiments, any leg movement will be restricted as much as possible, using padding and immobilization devices. The knee joint may foe centered in a knee MRI coil, and the coil may be positioned as close to isocenter as possible.

In some embodiments, the information received at step 102 may include data sufficient to correlate a position and orientation of a mechanical axis of the patient's leg to the imaging data of the patient's joint of interest. This additional data may be obtained by an x-ray of the patient's full leg (including the hip and ankle joints) or in other manners, such as a full length MRI or CT.

In the particular embodiment shown, the information received at step 102 also may include other information about the patient and/or the surgeon's preferences about the orthopedic procedure. Such additional information may include: information identifying the patient, identifying the surgeon, acceptable tolerances to the surgeon (e.g. amount of overhang/underhang permissible for implant coverage fit), relative importance of various orthopedic responses to the surgeon (discussed further below), surgeon preferences regarding varus/valgus alignment, femoral rotation, implant position and orientation, resections, sizing (upsize, downsize), soft and hard tissues analysis, bone strength DXA scores, hormone/blood markers levels, demographic information (including age, sex/gender, race/ethnicity), past medical history and comorbidities, smoking, allergies, hormonal status, hormone medications, genetics/family history, etc.

The "enhanced" patient data set may be part of the same step as step 102 or a separate step. The data received may reflect information that is not included in the standard patient data received at step 102 but that is used in the processes of FIG. 11. This enhanced data may include, without limitation, data reflecting the patient's gait, foot mechanics, patient anthropometrics, patient lifestyle (e.g. level of activity, types of common activities, etc.), physiological attributes (e.g. collagen levels in tissue as indicator of ligament strength), presence and characterization of previous injuries, co-morbidity data concealing other joint functionality or lack thereof, or other types of data about the patient.

In some embodiments, the standard and enhanced data sets received in steps 102 may be collected using a web or other computer based interface allowing a user, such as a surgeon, doctor's assistant, or other user, to input and/or upload this data. Other data collection methods may also be utilized. In some embodiments, the types of data collected may change. For instance, in some embodiments, algorithms used for the biomechanic and anatomic fit optimizers may be updated such that different types of enhanced data are required for inputs to the optimizers, which, again, are discussed in further detail below. In such instances, the data collection interface, whether web based or otherwise, may be quickly and easily updated to reflect the different information needed.

Step 104 is an optional step and may be omitted in some embodiments. In step 104, the raw image data is filtered and enhanced. As examples, the raw image data may be smoothed, edges may be enhanced, the data may be filtered according to gray scale, gradient, or combinations thereof.

Returning to FIG. 1, in step 106 the image data may be processed to create a three dimensional model (e.g. a CAD model) of the patient's joint or at least portions thereof. The three dimensional model may be created by segmenting or otherwise processing the imaging data to reconstruct the geometry and shape, or otherwise define the relevant, surfaces and other morphological aspects of the patient's anatomy. Such segmenting may be accomplished by manual, automated, or semi-automated processes. In some embodiments, segmentation may be facilitated by software packages available from, for instance, Able Software Corp of Lexington, Mass. (3D-doctor). Materialise of Leuven, Belgium (Mimics), Boykov/Kolmogorov Max Flow algorithm, or other software. In some embodiments, other techniques may be used to process imaging data, such as threshold based image processing, probabilistic atlas based, statistical shape modeling based, or other techniques. Some embodiments may at least partially utilize Marlab based processes (of MathWorks, Inc., Natick, Mass.) as part of such techniques.

In step 108, the volume data is converted to surface data to create the polygonal representation. As examples, the conversion may occur using the CRUST algorithm or MARCHING CUBES algorithm.

Step 110 is an optional step and may be omitted in some embodiments. In step 110 the surface model may be post-processed. Post-processing typically includes surface editing, hole filling, decimation, and smoothing. Due to the voxelated nature of the model creation, some artifacts appear in the initial geometry. Smoothing removes these artifacts while preserving volume to allow for a more realistic appearance and to facilitate downstream processes that rely on smooth surfaces. Decimation is the process by which the overall number of triangles is reduced to allow for faster processing. As an example, all or part of the post-processing step may be accomplished using the software GEOMAGIC STUDIO. GEOMAGIC STUDIO is a registered trademark of Geomagic, Inc. of Research Triangle Park, N.C.

In some embodiments, a model of the patient's joint may be created by identifying a set of points and/or dimensions in or from the image data rather than segmenting the joint surfaces in detail. For instance, in some embodiments, only certain key reference points and/or dimensions are necessary inputs to the optimization sub-processes described below, and, thus, only these reference points and dimensions need to be identified from the patient specific data (whether image or other types of data).

In some embodiments, the imaging data or other information concerning the patient may be processed to identify additional qualitative or quantitative information for incorporation into or other use with the three dimensional model, such as, but not limited to, a position and/or orientation of the mechanical axis of the patient's leg relative to the three dimensional joint model and other reference frame information (e.g. identification of particular reference points, axes or other constructs with respect to the three-dimensional anatomic model). In some embodiments, the mechanical ax is of the leg and its relationship to the model of the patient's knee can be determined by overlaying a full leg x-ray of the patient on the three dimensional model.

At step 106, the imaging data may also be processed to identify ligamentous tissue, ligament attachment locations, and/or other soft tissue attachment locations relative to the three dimensional model, in some embodiments, step 106 may be performed simultaneously or otherwise in conjunction with other processing done to the MRI data. Moreover, as with the segmentation processes, identification of the ligament attachment locations may be done manually, semi-automatically, or using fully automated functionality.

In some embodiments, the image data and other information received concerning the particular patient may be further processed such that the three dimensional model incorporates or otherwise reflects other information, such as information relating to mechanical properties of bone (e.g. bone density), cartilage and soft tissues.

Figure 2:
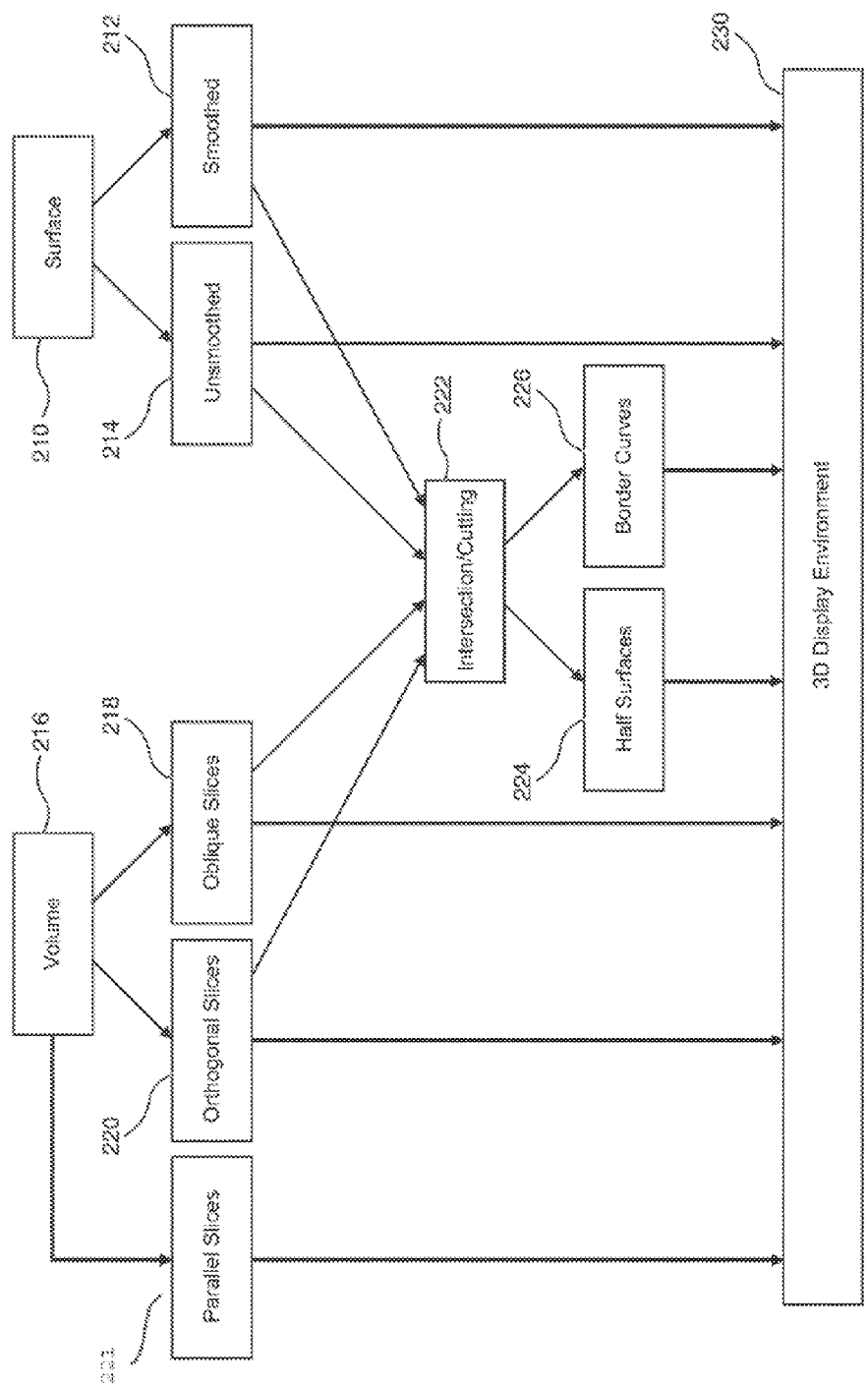
FIG. 2 shows an illustrative overview of the software elements for displaying both volume data and surface data.

FIG. 2 illustrates an overview of the software elements for displaying both surface data 210 and volume data 216 in a display environment 230 according to certain embodiments. In the depicted embodiment, surface data 210 includes both smoothed data 212 and unsmoothed data 214. In certain embodiments, the surface data 210 may include only smoothed data 212 or only unsmoothed data 214. The volume data 216 is the raw or preprocessed image data. In certain embodiments, these are MRI data slices in the sagittal plane that are spaced apart from one another a set distance, such as 2 mm. Alternatively, the raw image data may be MRI data slices in the coronal plane or the transverse plane that are spaced apart from one another a set distance. In yet another embodiment, the raw image data may be MRI data slices taken at an oblique angle that are spaced apart from one another a set distance. Whether the raw image data is sagittal, coronal, transverse, or oblique, it merely provides a frame of reference for the interpolated slices. The term "original" means the plane of reference in which the raw image data was taken, whether that is sagittal, coronal, transverse, or oblique. The volume data 216 is used to create interpolated parallel slices 221, interpolated orthogonal slices 220, and interpolated oblique slices 218. The term "orthogonal" means the created slice is orthogonal to the original plane. The term "oblique" means the created slice is oblique to the original plane. The term "parallel" means the created slice is parallel to the original plane. The oblique slice is said to be oblique to the raw image data because it is oblique to a plane of reference in which the raw image data was taken. In some embodiments, the orthogonal and oblique slices may be calculated and stored in a database. In the depicted embodiments, the orthogonal and oblique slices are created in real time for display.

In portion 222, the volume data 216 and surface data 210 is manipulated to create intersections or cuts for displaying only portions of the surface data 210. The orthogonal slice "cuts" the smoothed data 212 and the unsmoothed data 214. Further, the oblique slice "cuts" the smoothed data 212 and the unsmoothed data 214. The portion 222 is then used to create the half surfaces 224 and the border curves 226.

A user manipulates the display environment 230. The user has the option to display one or more of: the original slice, an interpolated parallel slice, an interpolated orthogonal slice, an interpolated oblique slice, a half surface, a border curve, unsmoothed surface data, and smoothed surface data. For example, each part of the display environment may be on a layer and the user may turn on or off selected layers. By turning on key layers, a user may visualize key portions of anatomy or landmarks. As the surface model is created from the volume data, both data sets have the same coordinated system and are, therefore, automatically registered with one another. The volume data and the surface model can thus be displayed together as an integrated image.

FIG. 3 illustrates a software program 314 for creating slices and intersecting the created slices with the surface data according to certain embodiments. The software program 314 may be written any of the numerous computing languages, such as C++, Java, Python, PERL, or TCL. The program 314 accesses the volume data 310 and the surface data 312. The program 314 uses user provided information to create in real lime an interpolated parallel slice, an interpolated oblique slice, and/or an interpolated orthogonal slice using interpolation. The program 314 then calls an application programming interface (API) 316. In the depicted embodiment, the API is the Visualization Toolkit (VTK) algorithm but other algorithms may be used. At 318, the API provides functionality to intersect the created slice with the surface model and sends the resultant model to the display environment 230.

Figure 5:
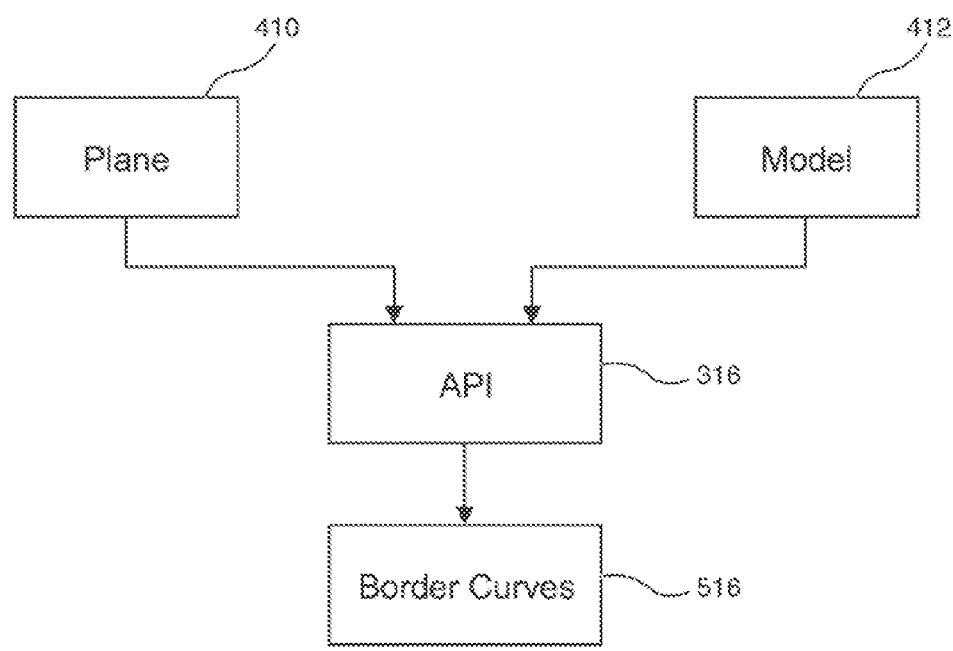

Additional details of the API are illustrated in FIGS. 4 and 5. The API 316 is used to intersect the created slice 410 with a portion of the surface data 312, such as a model 412. In the depicted embodiment, the VTK algorithm executes the "cutter" operation. This results in a model with two parts: Model + 416 and Model − 418. The models 416, 418 are sent to program 314, which selects one of them, based on user view orientation, to display 318.

As shown in FIG. 5, the API also creates border curves 516 to highlight edges of the model after intersection according to certain embodiments. The API 316 computes the intersection of the created slice 410 with the model 412 to create border curves 516. In the depicted embodiment, the VTK algorithm executes the "stripper" operation. The API 316 sends the border curves 516 to the program 314.

Figure 6:
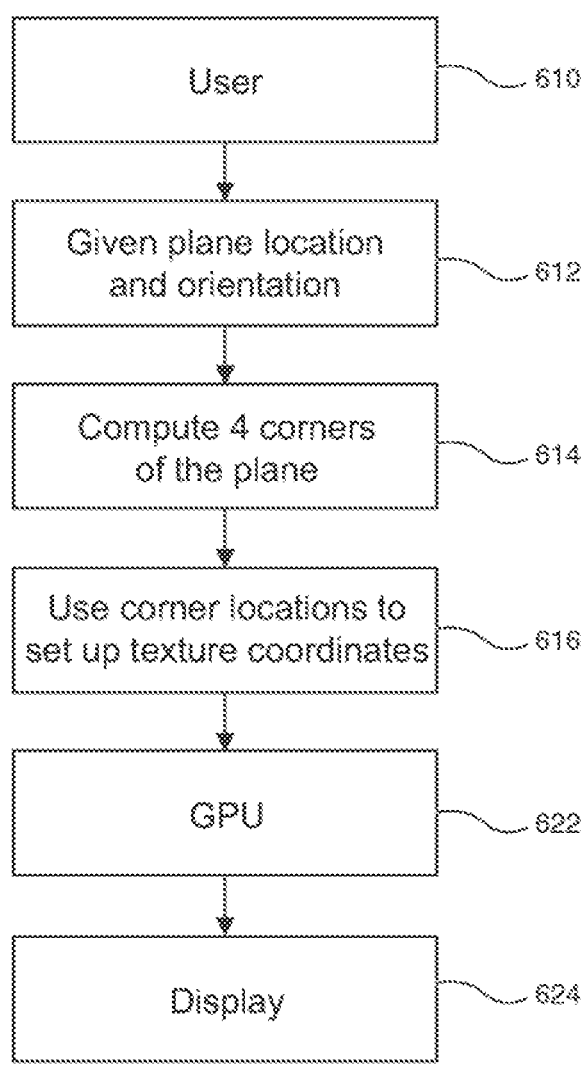
FIG. 6 show an illustrative overview of the user interaction with a display environment.

FIG. 6 illustrates an overview of the user interaction with the display environment according to certain embodiments. A user turns on or off selected layers in step 610. The user selects a plane location and orientation in step 612. This may be done with a keyboard, touchscreen, or a mouse. For example, a user may zoom and/or rotate the model to select a viewing plane. The four corners of the plane are calculated in step 614. Texture coordinates are set up in step 616. The volume and surface data are then processed in step 622 using the software elements shown in FIGS. 3-5. Step 622 is performed using the graphical processing unit (GPU). In some embodiments, however, the central processing unit (CPU) may be used instead. The GPU sends the output to the display environment in step 624.

Figure 7:
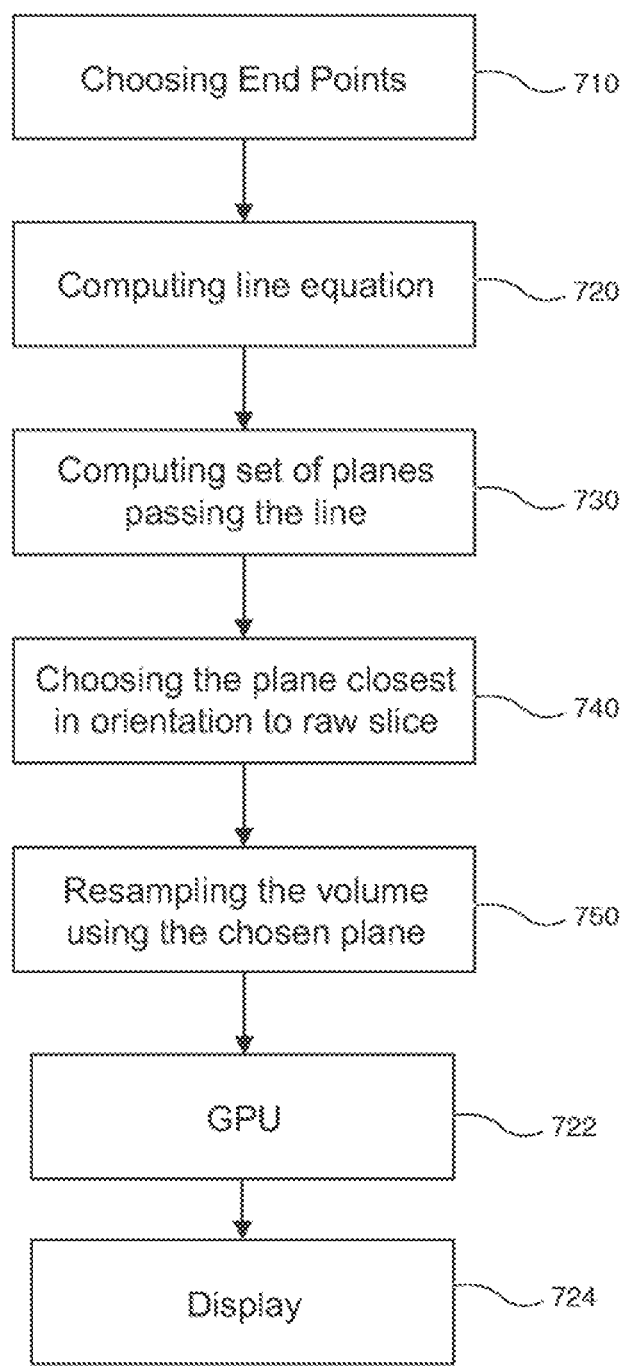
FIG. 7 illustrates one example for displaying both volume and segmentation data.

FIG. 7 illustrates one example for displaying both volume and segmentation data according to certain embodiments. The user chooses end points in step 710 to draw a line. The line may define an area of anatomical interest or provide a rotation of axis. As an example, each end of the line may be a landmark, such as the femoral epicondyle. The user selects the endpoints using the mouse, touchscreen, and/or keyboard. The line equation is computed in step 720. A set of planes passing through the line are calculated in step 730. In step 740, the plane closest in orientation to the raw slice is determined and selected. The volume is resampled in step 750 using the selected plane. The resampled volume is sent to the GPU in step 722 and displayed in step 724.

Figure 8A:
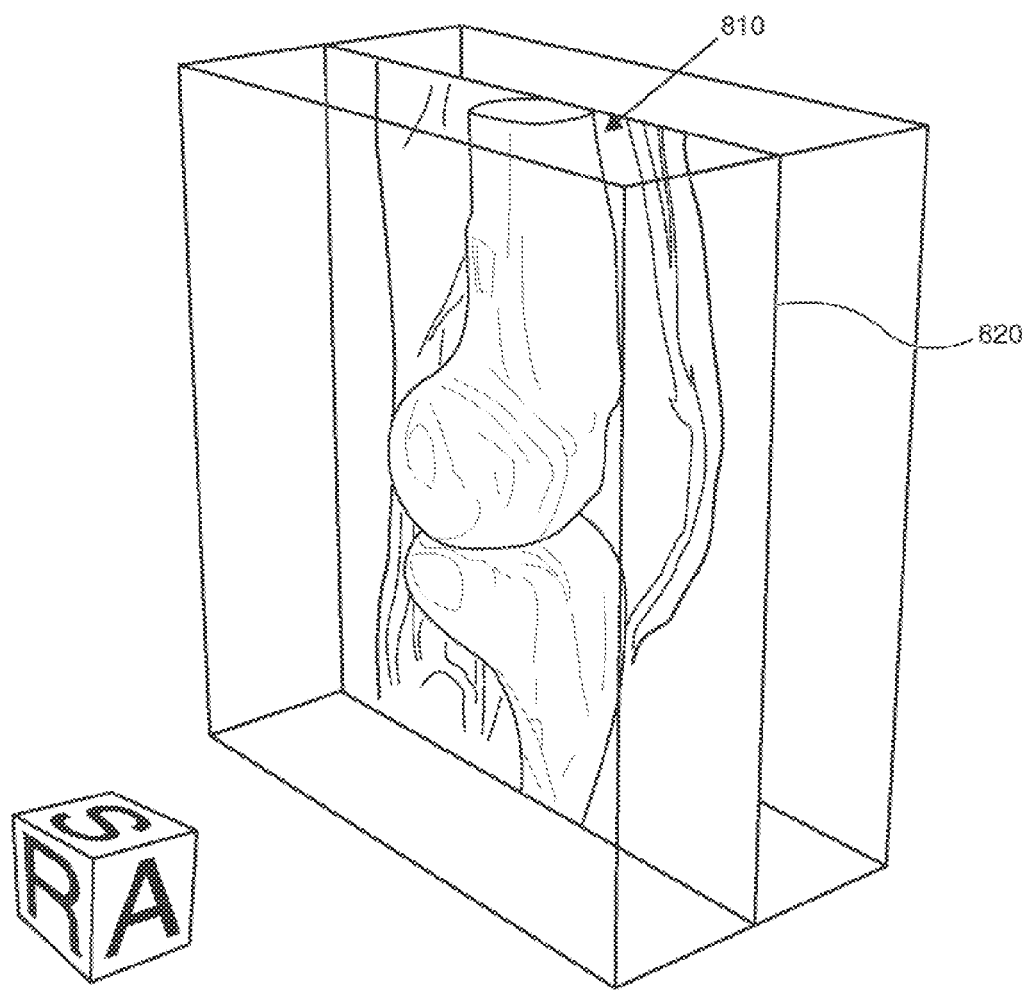
FIG. 8A-8F illustrate examples of the display environment of FIG. 6.
Figure 8B:
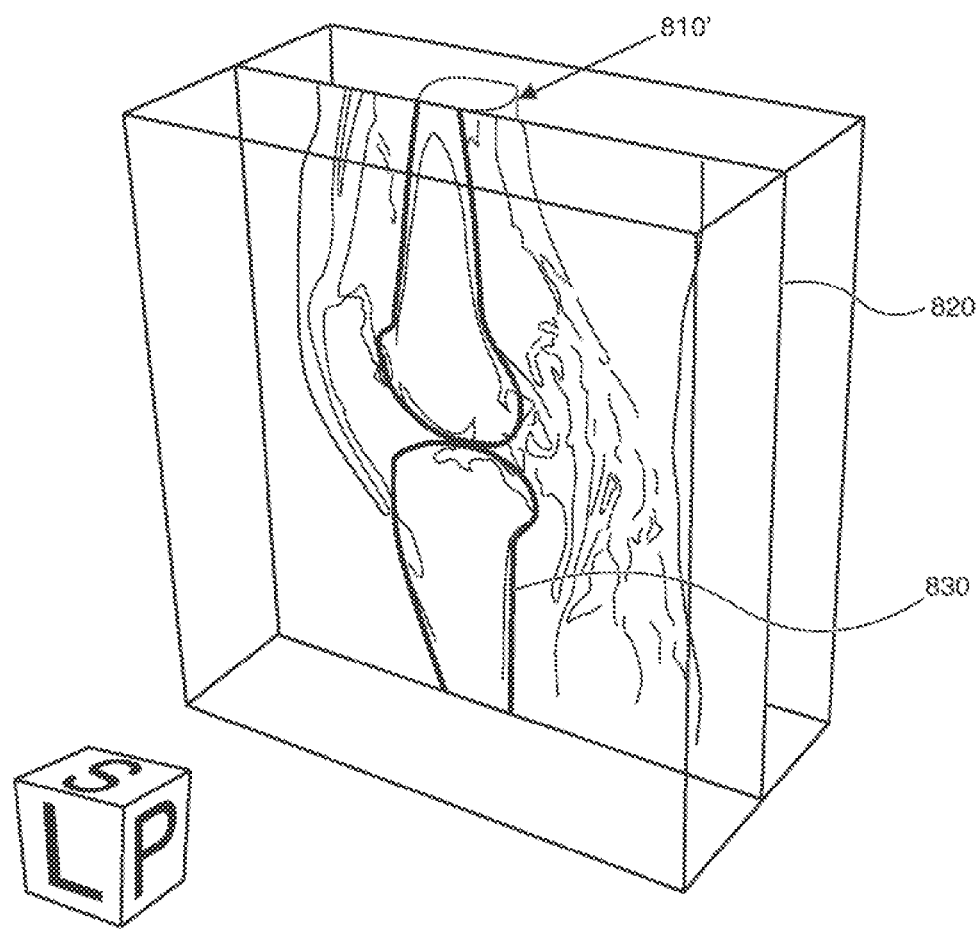
Figure 8C:
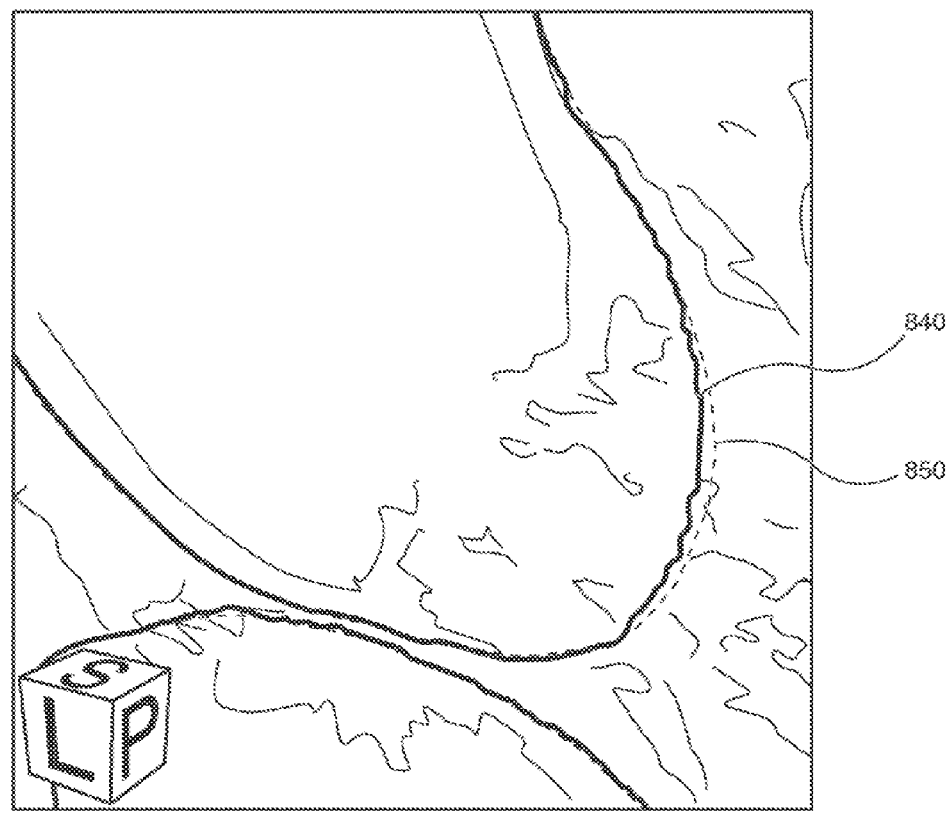
Figure 8D:
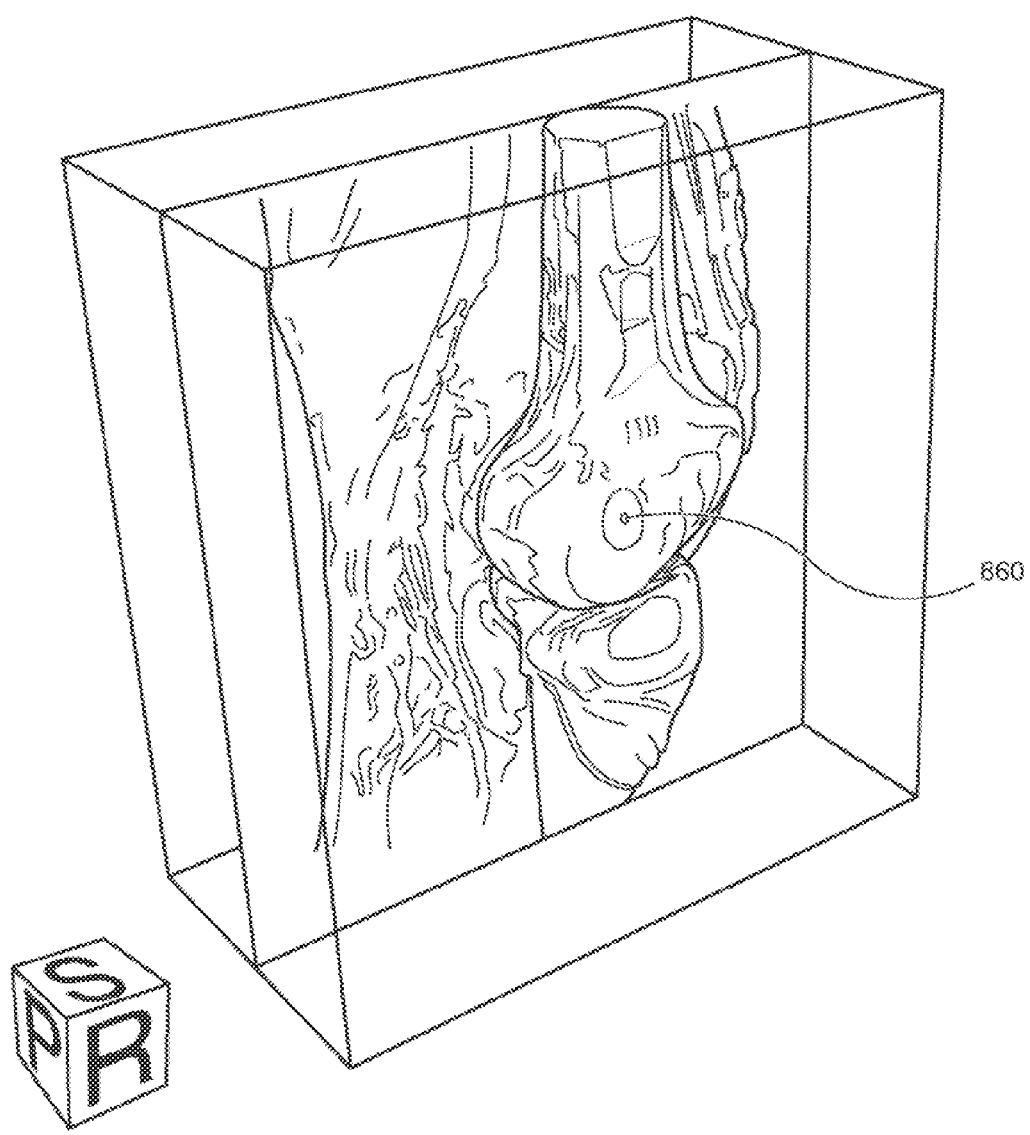
Figure 8E:
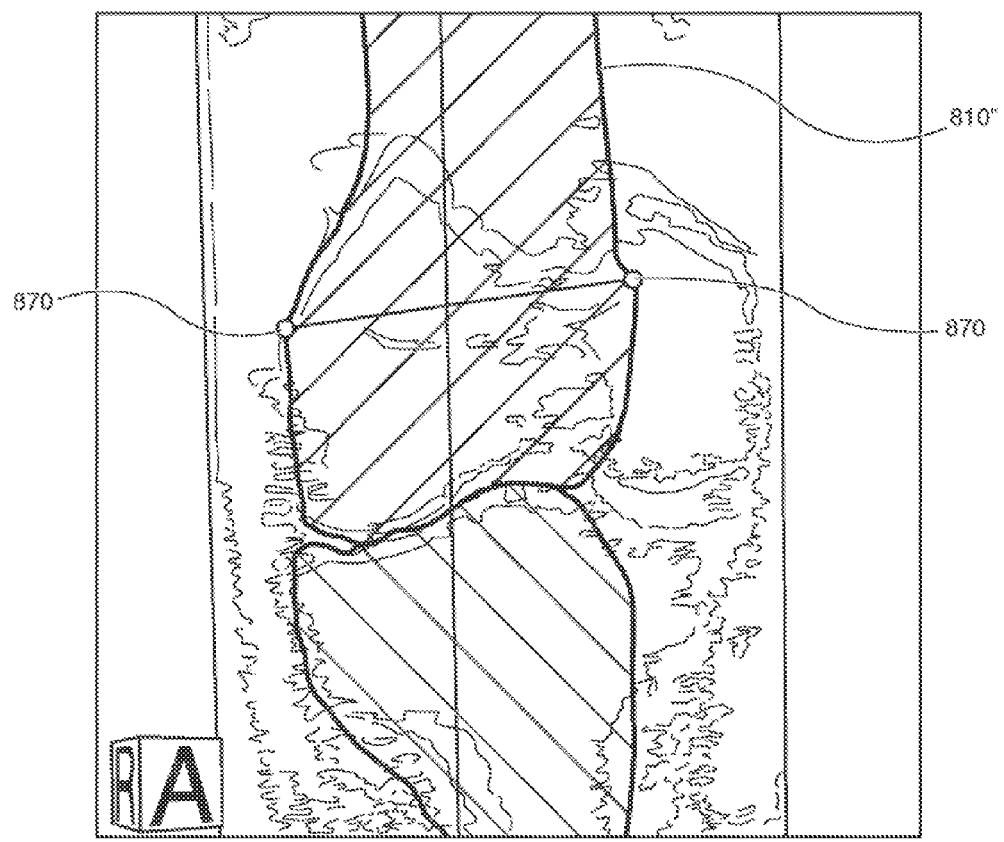
Figure 8F:
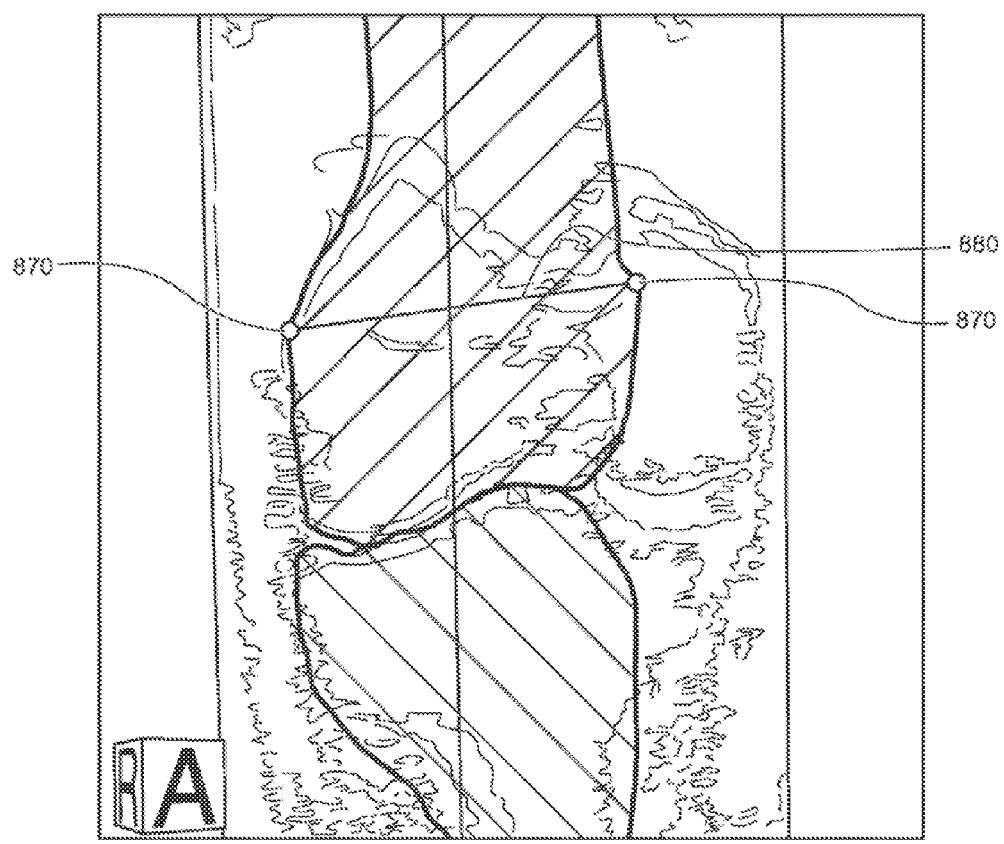

FIGS. 8A-8F illustrate examples of the display environment of FIG. 6 according to certain embodiments. In FIGS. 8A-8F, there is a marker near the figure in which: S is the superior direction, R is the right side, A is the anterior side, L is the left side, and P is the posterior side. The marker shows the orientation in the anatomic context. In FIG. 8A, the program displays both the surface model 810 and the volume data 820, such as an MRI slice, together as an integrated image. In FIG. 8B, the image plane 820 cuts the surface model 810 so half of the surface is removed. This results in modified surface model 810' with border curves 830, allowing evaluation of the boundaries where the image plane and surface model intersect. FIG. 8C illustrates a close-up view of the border curves of the model from raw, unsmoothed data 840 and smoothed data 850. This can be used to evaluate the error introduced by smoothing and/or errors during segmentation. In FIG. 8D, a landmark point 860 is picked by a user on the surface model. FIG. 8E illustrates two landmark points 870 selected by a user to determine a rotation axis, for display together with a half surface model. In the depicted example, the half surface models are bone models of a femur and a tibia. In FIG. 8F, the landmark points 870 and the axis 880 are displayed in conjunction with the oblique 2D slice.

In an alternative embodiment, the same software program is extended to allow the users to segment structures from any of the orthogonal/oblique slices. The same software program is used to evaluate the effect of smoothing the surface using a third party tool.

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in knee arthroplasty, may be applied to systems, devices, and methods to be used in other surgical procedures including, but not limited to, spine arthroplasty, cranio-maxillofacial surgical procedures, acetabular systems, shoulder arthroplasty, as well as foot, ankle, hand, and extremities procedures.

Variations and modifications will occur to those of skill in the art after reviewing this disclosure. The disclosed features may be implemented, in any combination and subcombination (including multiple dependent combinations and sub-combinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. A system for determining an accuracy of a bone model, comprising:
   at least one processor; and
   at least one memory having a plurality of instructions stored thereon that, in response to execution by the at least one processor, causes the system to:
      create a three-dimensional surface model of a portion of a patient's joint based on raw image data of the patient's joint;
      determine a border curve defined by an intersection of an image plane and the three-dimensional surface model of the portion of the patient's joint; and
      compare an intersection of the raw image data of the patient's joint and the image plane with the determined boundary curve to evaluate an accuracy of the three-dimensional surface model.

2. The system of claim 1, wherein to create the three-dimensional surface model comprises to:
   generate a three-dimensional volume image from a set of magnetic resonance imaging (MRI) data slices; and
   create the three-dimensional surface model based on the three-dimensional volume image.

3. The system of claim 2, wherein the three-dimensional surface model is a polygonal representation of the patient's joint.

4. The system of claim 2, wherein to create the three-dimensional volume image comprises interpolation of the raw image data.

5. The system of claim 1, wherein to create the three-dimensional surface model comprises to:
generate a three-dimensional volume image based on a set of points identified in the raw image data; and
create the three-dimensional surface model based on the three-dimensional volume image.

6. The system of claim 1, wherein to create the three-dimensional surface model comprises to
filter the raw image data to generate smoothed image data;
generate a three-dimensional volume image based on the smoothed image data; and
create the three-dimensional surface model based on the three-dimensional volume image; and
wherein the accuracy of the three-dimensional surface model is based on errors introduced by at least one of filtering the raw image data or generating the three-dimensional volume image.

7. The system of claim 1, wherein the raw image data is volume data.

8. A method for determining an accuracy of a bone model, comprising:
creating a three-dimensional surface model of a portion of a patient's joint based on raw image data of the patient's joint;
determining a border curve defined by an intersection of an image plane and the three-dimensional surface model of the portion of the patient's joint; and
comparing an intersection of the raw image data of the patient's joint and the image plane with the determined boundary curve to evaluate an accuracy of the three-dimensional surface model.

9. The method of claim 8, wherein creating the three-dimensional surface model comprises:
generating a three-dimensional volume image from a set of magnetic resonance imaging (MRI) data slices; and
creating the three-dimensional surface model based on the three-dimensional volume image.

10. The method of claim 9, wherein the three-dimensional surface model is a polygonal representation of the patient's joint.

11. The method of claim 9, wherein creating the three-dimensional volume image comprises interpolating the raw image data.

12. The method of claim 8, wherein creating the three-dimensional surface model comprises:
generating a three-dimensional volume image based on a set of points identified in the raw image data; and
creating the three-dimensional surface model based on the three-dimensional volume image.

13. The method of claim 8, wherein creating the three-dimensional surface model comprises:
filtering the raw image data to generate smoothed image data;
generating a three-dimensional volume image based on the smoothed image data; and
creating the three-dimensional surface model based on the three-dimensional volume image; and
wherein the accuracy of the three-dimensional surface model is based on errors introduced by at least one of filtering the raw image data or generating the three-dimensional volume image.

14. The method of claim 8, wherein the raw image data is volume data.

15. The method of claim 14, further comprising displaying the volume data and the three-dimensional surface model as an integrated image.

16. The method of claim 8, wherein the raw image data is captured along one of a transverse plane, a sagittal plane, or a coronal plane of the patient.

17. One or more non-transitory machine-readable storage media comprising a plurality of instructions stored thereon that, in response to execution by a computing device, causes the computing device to:
create a three-dimensional surface model of a portion of a patient's joint based on raw image data of the patient's joint;
determine a border curve defined by an intersection of an image plane and the three-dimensional surface model of the portion of the patient's joint; and
compare an intersection of the raw image data of the patient's joint and the image plane with the determined boundary curve to evaluate an accuracy of the three-dimensional surface model.

18. The one or more non-transitory machine-readable storage media of claim 17, wherein to create the three-dimensional surface model comprises to:
generate a three-dimensional volume image from a set of magnetic resonance imaging (MRI) data slices; and
create the three-dimensional surface model based on the three-dimensional volume image.

19. The one or more non-transitory machine-readable storage media of claim 17, wherein to create the three-dimensional surface model comprises to:
generate a three-dimensional volume image based on a set of points identified in the raw image data; and
create the three-dimensional surface model based on the three-dimensional volume image.

20. The one or more non-transitory machine-readable storage media of claim 17, wherein to create the three-dimensional surface model comprises to:
filter the raw image data to generate smoothed image data;
generate a three-dimensional volume image based on the smoothed image data; and
create the three-dimensional surface model based on the three-dimensional volume image,
wherein the accuracy of the three-dimensional surface model is based on errors introduced by at least one of filtering the raw image data or generating the three-dimensional volume image.

* * * * *